United States Patent
Dickie et al.

(10) Patent No.: US 10,646,196 B2
(45) Date of Patent: May 12, 2020

(54) SYSTEMS AND METHODS FOR DETERMINING A HEART RATE OF AN IMAGED HEART IN AN ULTRASOUND IMAGE FEED

(71) Applicant: Clarius Mobile Health Corp., Burnaby (CA)

(72) Inventors: Kris Dickie, Vancouver (CA); Nishant Uniyal, Vancouver (CA); Narges Afsham, Coquitlam (CA); Laurent Pelissier, North Vancouver (CA)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 340 days.

(21) Appl. No.: 15/597,087

(22) Filed: May 16, 2017

(65) Prior Publication Data

US 2018/0333134 A1    Nov. 22, 2018

(51) Int. Cl.
*A61B 8/02* (2006.01)
*A61B 8/00* (2006.01)
(Continued)

(52) U.S. Cl.
CPC .............. *A61B 8/02* (2013.01); *A61B 8/469* (2013.01); *A61B 8/5223* (2013.01);
(Continued)

(58) Field of Classification Search
CPC ......... A61B 8/02; A61B 8/469; A61B 8/5223; G06T 2207/10016; G06T 2207/10132;
(Continued)

(56) References Cited

U.S. PATENT DOCUMENTS 5,442,940 A * 8/1995 Secker ..................... A61B 8/02
   600/453
5,515,856 A   5/1996 Olstad et al.
(Continued)

FOREIGN PATENT DOCUMENTS

EP       1967867 A2    9/2008
WO    2015049609 A1    4/2015

OTHER PUBLICATIONS

Zahorian, An Enhanced Signal Processing Strategy for Fetal Heart Rate Detection, May 1996 (Year: 1996).*

(Continued)

*Primary Examiner* — Peter Luong
(74) *Attorney, Agent, or Firm* — Julian Ho

(57) ABSTRACT

The present embodiments relate generally to systems, methods, and apparatus for determining a heart rate of an imaged heart in an ultrasound image feed. A plurality of ultrasound images can first be acquired. For each ultrasound image of the plurality of ultrasound images, the image can be divided into a plurality of regions; where each region is positioned so that the region corresponds to a substantially similar region location present across the plurality of ultrasound images. For each region location on each of the plurality of ultrasound images, a statistical calculation on image data of the region location can be performed. For each region location, a frequency of change in the statistical calculation over the plurality of ultrasound images can then be determined. The region location having a dominant determined frequency of change in the statistical calculation (over the plurality of ultrasound images) can be identified as a region of interest (ROI). The heart rate can be calculated based on the determined frequency of change of the ROI.

20 Claims, 8 Drawing Sheets

(51) Int. Cl.
*A61B 8/08* (2006.01)
*G06T 7/00* (2017.01)
*G06T 7/254* (2017.01)

(52) U.S. Cl.
CPC ............ *G06T 7/0012* (2013.01); *G06T 7/254* (2017.01); *G06T 2207/10016* (2013.01); *G06T 2207/10132* (2013.01); *G06T 2207/20021* (2013.01); *G06T 2207/20056* (2013.01); *G06T 2207/30048* (2013.01)

(58) Field of Classification Search
CPC . G06T 2207/20021; G06T 2207/20056; G06T 2207/30048; G06T 7/0012; G06T 7/254
See application file for complete search history.

(56) References Cited

U.S. PATENT DOCUMENTS

| | | | |
|---|---|---|---|
| 6,312,382 | B1 | 11/2001 | Mucci et al. |
| 7,695,439 | B2 | 4/2010 | Jackson et al. |
| 7,775,978 | B2 | 8/2010 | Nadadur et al. |
| 2003/0016852 | A1* | 1/2003 | Kaufman ............ A61B 5/0456 382/131 |
| 2004/0152983 | A1 | 8/2004 | Vince et al. |
| 2006/0079783 | A1 | 4/2006 | Clark |
| 2006/0241457 | A1* | 10/2006 | Nadadur ............ A61B 5/02028 600/450 |
| 2007/0016019 | A1 | 1/2007 | Salgo |
| 2007/0255139 | A1 | 11/2007 | Deschinger et al. |
| 2008/0125652 | A1 | 5/2008 | Clark |
| 2010/0185088 | A1 | 7/2010 | Perrey et al. |
| 2010/0198073 | A1* | 8/2010 | Nishihara ............ A61B 8/14 600/443 |
| 2013/0253319 | A1 | 9/2013 | Hamilton et al. |
| 2017/0224238 | A1* | 8/2017 | Arunachalam ........ A61B 5/046 |

OTHER PUBLICATIONS

Ibrahimy, M. I., et al. (2003). "Real-Time Signal Processing for Fetal Heart Rate Monitoring", in IEEE Transactions on Biomedical Engineering 50 (2), Feb. 2003.

Jezewski, J., Roj, D., Wrobel, J., and Horoba, K. (2011). "A novel technique for fetal heart rate estimation from Doppler ultrasound signal", in BioMedical Engineering OnLine 2011, 10:92.

Koninklijke Philips Electronics N.V. (2012). "Revolutionizing premium performance ultrasound", Philips iU22xMATRIX_WHC Brochure, Jan. 2012.

Abdulhay, E. W. et al. (2014). "Review Article: Non-Invasive Fetal Heart Rate Monitoring Techniques", in Biomedical Science and Engineering 2 (3), 53-67.

Shah, S. et al. (2014). "BE-SAFE: Bedside Sonography for Assessment of the Fetus in Emergencies: Educational Intervention for Late-pregnancy Obstetric Ultrasound", in Western Journal of Emergency Medicine, vol. XV, No. 6: Sep. 2014.

Lipton, M. et al. (2014). "Ultrasound: Focused 1st Trimester Pregnancy (Transabdominal Exam)", Academic Life in Emergency Medicine. Dec. 31, 2014.

Jurgens, J. and Chaoui, R. (2003). "Three-dimensional multiplanar time-motion ultrasound or anatomical M-mode of the fetal heart: a new technique in fetal echocardiography", in Ultrasound Obstet Gynecol 2003; 21: 119-123.

* cited by examiner

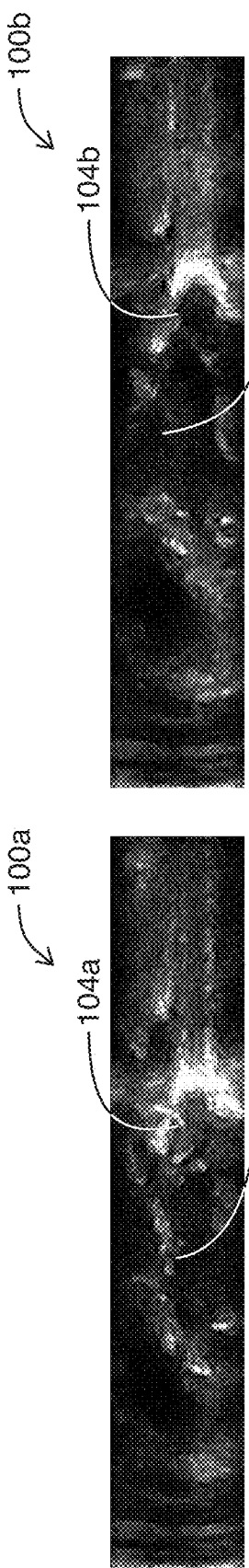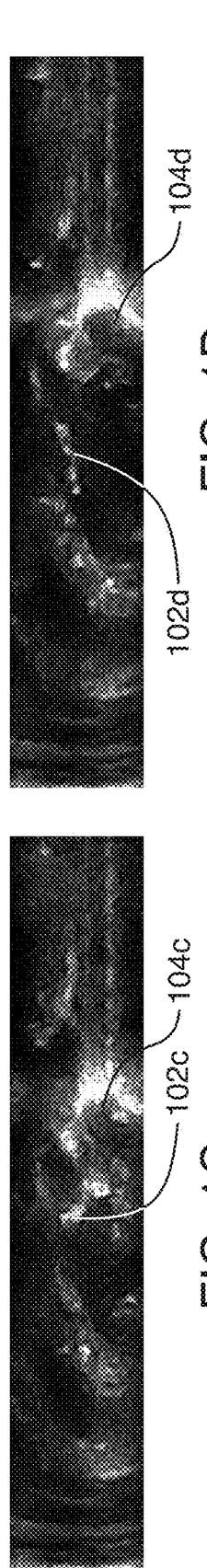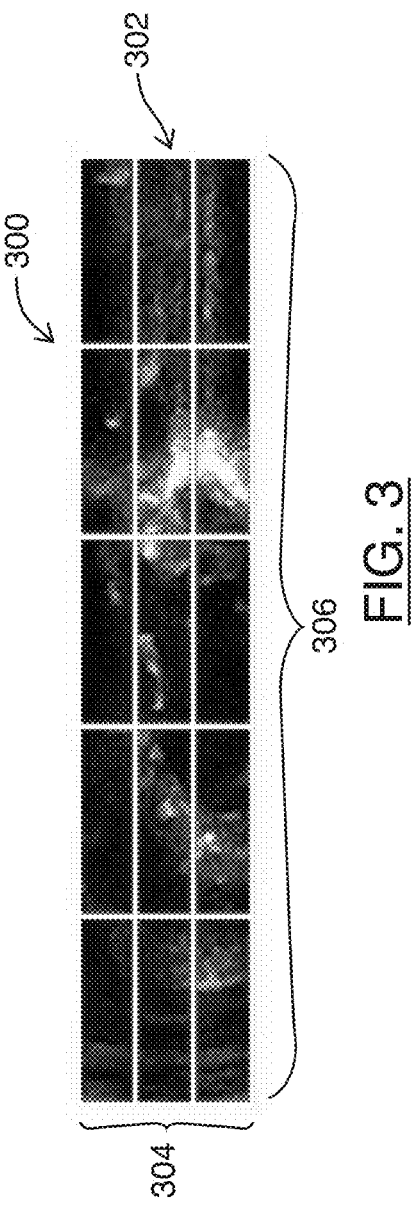

SYSTEMS AND METHODS FOR DETERMINING A HEART RATE OF AN IMAGED HEART IN AN ULTRASOUND IMAGE FEED

FIELD

The present disclosure relates generally to ultrasound imaging, and in particular, systems and methods for determining a heart rate of an imaged heart in an ultrasound image feed.

BACKGROUND

Ultrasound imaging systems are a powerful tool for performing real-time imaging procedures in a wide range of medical applications. When performing standard imaging, ultrasound systems are typically operated in brightness-mode (commonly known as B-mode). When using B-mode to perform cardiac imaging, the motion of a heart beating can be viewed.

Traditionally, to measure the heart rate of an imaged heart, an ultrasound operator may select the system to be operated in motion-mode (commonly called M-mode). In M-mode, a single scan line is placed along an area of interest, and imaging along that one scan line is successively displayed along the X-axis over time. When there is motion along the scan line (e.g., when the scan line is placed so that it traverses the wall of a heart as it moves towards and away from the probe head), the resultant M-mode image appears as if it has a waveform that reflects the motion over time. A peak-to-peak measurement of this waveform can provide a heart rate measurement (after the sampling rate of the ultrasound image feed is taken into account).

M-mode may be cumbersome to use. For example, selecting the initial scan line and/or measuring the peak-to-peak distance may take time and expertise. As a result, there have been attempts to automate heart rate determination during B-mode imaging. These attempts typically involve automating manual M-mode processes. For example, in one scenario, a scan line is automatically selected and a time-series is generated over a series of frames at this scan line. A spectral analysis (such as a Fourier transform) is then performed on the data in the time-series to identify a frequency that may be reflective of the heart rate. Since this method relies on automated selection of a scan line, it may fail to capture motion in heart anatomical structures on areas of the image that do not intersect the scan line.

In another example, spatial points are identified on an image, and image data at these spatial points are plotted with respect to time. A Fourier transform may then be performed on the plotted image data to identify the heart rate. Since this method performs Fourier transform on the image data itself, it is similar to M-mode analyses and relies on plotted image data having a waveform appearance for the Fourier transform to accurately identify a frequency. However, such methods may not be sufficiently robust to determine a heart rate in situations where the image data at a selected spatial point plotted over time does not produce a waveform appearance (e.g., where a heart valve is present on a spatial point when it is closed, but not present on that spatial point when the heart valve is open, so that the resultant plotted image data over time does not produce a waveform).

There is thus a need for improved systems for determining a heart rate of an imaged heart in an ultrasound image feed. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which:

FIGS. 1A-1D are selected frames of an example ultrasound image feed containing an imaged heart, in accordance with at least one embodiment of the present invention;

FIG. 3 is an illustration of regions that may be positioned on frames of an ultrasound image feed having an imaged heart, in accordance with at least one embodiment of the present invention;

DETAILED DESCRIPTION

Figure 2:
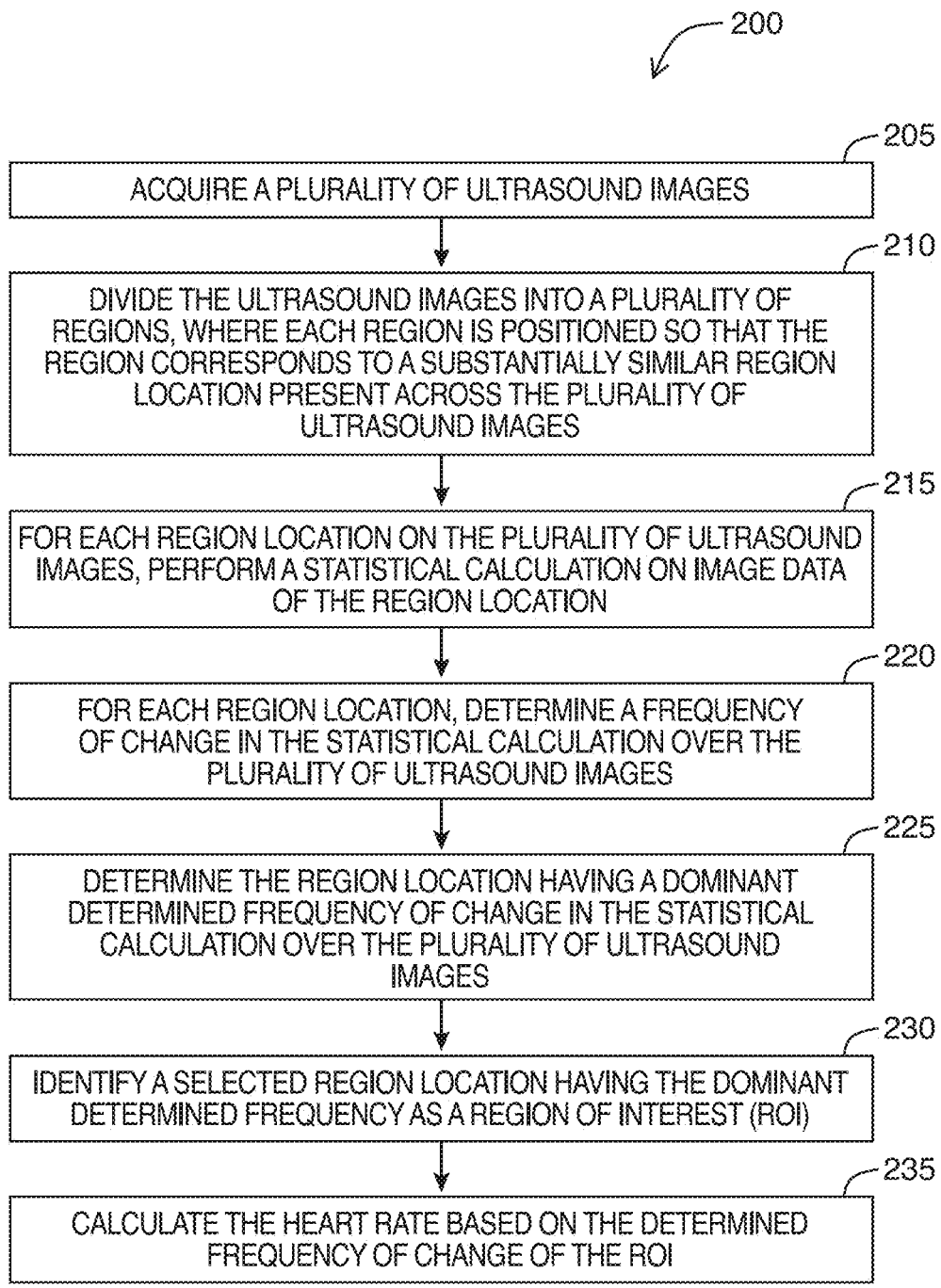
FIG. 2 is a flowchart for a method of determining a heart rate of an imaged heart in an ultrasound image feed, in accordance with at least one embodiment of the present invention.

In a first broad aspect of the present disclosure, there is provided a method of determining a heart rate of an imaged heart in an ultrasound image feed. The method may involve: acquiring a plurality of ultrasound images; for each ultrasound image of the plurality of ultrasound images, dividing the image into a plurality of regions, wherein each region is positioned so that the region corresponds to a substantially similar region location present across the plurality of ultrasound images; for each region location on each of the plurality of ultrasound images, performing a statistical calculation on image data of the region location; for each region location, determining a frequency of change in the statistical calculation over the plurality of ultrasound images; determining the region location having a dominant determined frequency of change in the statistical calculation over the plurality of ultrasound images; identifying a selected region location having the dominant determined frequency as a region of interest (ROI); and calculating the heart rate based on the determined frequency of change of the ROI.

In some embodiments, the statistical calculation includes an indication of variation in brightness of the image data of the region location. In some embodiments, the statistical calculation includes a standard deviation of brightness values of the image data of the region location.

In some embodiments, when determining the frequency of change for each region location over the plurality of ultrasound images, the method further includes: performing a Fourier transform on the statistical calculations of the region location across the plurality of ultrasound images, to generate a power spectrum; and selecting a peak frequency from the power spectrum as the frequency of change for the region location.

In some embodiments, when determining the region location having the dominant determined frequency of change in the statistical calculation, the method further includes: selecting the region location, of the plurality of regions, having the highest magnitude for the frequency of change.

In some embodiments, the method further includes: prior to the dividing, scaling down at least one ultrasound image of the plurality of ultrasound images.

In some embodiments, the plurality of regions forms a grid. In some embodiments, a total number of region locations is less than fifty (50). In some embodiments, a total number of region locations is at least two (2).

In some embodiments, the method further includes performing a band pass filter on at least one determined frequency of a region location to eliminate non-heart-rate frequencies.

In some embodiments, the calculating the heart rate includes: translating the dominant determined frequency of change from a per-frame basis to a per-unit-time basis, and wherein the translating is performed based on a frame rate of the ultrasound image feed.

In another broad aspect of the present disclosure, there is provided an ultrasound imaging apparatus for determining a heart rate of an imaged heart in an ultrasound image feed, the apparatus including a processor, and a memory storing instructions for execution by the processor. When the instructions are executed by the processor, the processor can be configured to: acquire a plurality of ultrasound images; for each ultrasound image of the plurality of ultrasound images, divide the image into a plurality of regions, wherein each region is positioned so that the region corresponds to a substantially similar region location present across the plurality of ultrasound images; for each region location on each of the plurality of ultrasound images, perform a statistical calculation on image data of the region location; for each region location, determine a frequency of change in the statistical calculation over the plurality of ultrasound images; determine the region location having a dominant determined frequency of change in the statistical calculation over the plurality of ultrasound images; identify a selected region location having the dominant determined frequency as a region of interest (ROI); and calculate the heart rate based on the determined frequency of change of the ROI.

In some embodiments, the statistical calculation includes a standard deviation of brightness values of the image data of the region location.

In some embodiments, when determining the frequency of change for each region location over the plurality of ultrasound images, the processor is further configured to: perform a Fourier transform on the statistical calculations of the region location across the plurality of ultrasound images, to generate a power spectrum; and select a peak frequency from the power spectrum as the frequency of change for the region location.

In some embodiments, when determining the region location having the dominant determined frequency of change in the statistical calculation, the processor is further configured to: select the region location, of the plurality of regions, having the highest magnitude for the frequency of change.

In some embodiments, the processor is further configured to: prior to the dividing, scale down at least one ultrasound image of the plurality of ultrasound images.

In some embodiments, the processor is further configured to: perform a band pass filter on at least one determined frequency of a region location to eliminate non-heart-rate frequencies.

In another broad aspect of the present disclosure, there is provided a computer readable medium storing instructions for determining a heart rate of an imaged heart in an ultrasound image feed, the instructions for execution by a processor of a computing device. When the instructions are executed by the processor, the processor is configured to: acquire a plurality of ultrasound images; for each ultrasound image of the plurality of ultrasound images, divide the image into a plurality of regions, wherein each region is positioned so that the region corresponds to a substantially similar region location present across the plurality of ultrasound images; for each region location on each of the plurality of ultrasound images, perform a statistical calculation on image data of the region location; for each region location, determine a frequency of change in the statistical calculation over the plurality of ultrasound images; determine the region location having a dominant determined frequency of change in the statistical calculation over the plurality of ultrasound images; identify a selected region location having the dominant determined frequency as a region of interest (ROI); and calculate the heart rate based on the determined frequency of change of the ROI.

In some embodiments, the statistical calculation includes a standard deviation of brightness values of the image data of the region location.

In some embodiments, when determining the frequency of change for each region location over the plurality of ultrasound images, the instructions further configure the processor to: perform a Fourier transform on the statistical calculations of the region location across the plurality of ultrasound images, to generate a power spectrum; and select a peak frequency from the power spectrum as the frequency of change for the region location.

In another broad aspect of the present disclosure, there is provided another method of determining a heart rate of an imaged heart in an ultrasound image feed. The method may involve: acquiring a plurality of ultrasound images; calculating a difference between at least two successive images in the plurality of ultrasound images to determine pixel displacement of one or more pixel locations; optionally, performing a morphological operation to locate a region of interest (ROI) in the images where there is periodic motion; for the located ROI, performing a statistical calculation on image data of the region location over the plurality of ultrasound images; determining a frequency of change in the statistical calculation at the ROI over the plurality of ultrasound images; determining the dominant determined frequency of change in the statistical calculation at the ROI over the plurality of ultrasound images; and calculating the heart rate based on the determined dominant frequency of change at the ROI.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIGS. 1A-1D, shown there generally as 100a-100d are selected frames of an ultrasound image feed containing an imaged heart, in accordance with at least one embodiment of the present invention. The four frames 100a-100d are at different successive points in time over the series of frames. At the first point in time shown in FIG. 1A, a heart valve 102a can be seen in its closed position. As a cardiac cycle progresses, the heart valve would proceed to an open position, so that it would not be viewable in the same image location 102b at the subsequent point in time shown in FIG. 1B. As the cardiac cycle continues to progress, FIG. 1C and FIG. 1D show the heart valve 102c, 102d being restored to its closed position. Similarly, the heart wall 104a can be seen in FIG. 1A at the first point in time. Over the course of successive points in time shown in FIGS. 1B-1D, the heart wall positions 104b, 104c, 104d can be seen as relaxing and contracting during diastole and systole phases of the cardiac cycle. The example frames shown in FIGS. 1A-1D will be discussed below in the context of the methods described herein. For ease of illustration and discussion, the frames shown in FIG. 1A-1D are rotated '90' degrees from the orientation of their capture. However, it will be understood that the principles discussed herein may be applicable regardless of the orientation of the ultrasound image frames.

Referring to FIG. 2, shown there generally as 200 is a flowchart for a method of determining a heart rate of an imaged heart in an ultrasound image feed, in accordance with at least one embodiment of the present invention. In some embodiments, the various acts shown in FIG. 2 may be performed in real-time by an ultrasound system or machine (e.g., a functional block diagram of which is shown in FIG. 8). In some embodiments, the method of FIG. 2 may be performed on image frames of a stored cineloop containing video of an imaged heart. In such embodiments, portions of the cineloop may be considered an ultrasound image feed herein. In discussing the method of FIG. 2 below, reference will simultaneously be made to the image shown in FIG. 3, and the data plots shown in FIGS. 4-7.

At 205, the method involves acquiring a plurality of ultrasound images. For example, the ultrasound images may be acquired by transmitting and receiving ultrasound signals into tissue. As a person skilled in the art would understand, ultrasound image frames may be generated from these ultrasound signals. In various embodiments, a number of these images may be acquired and stored in memory so that the process of method of FIG. 2 may be performed on the stored images. In embodiments where the method of FIG. 2 is performed in real-time, a circular buffer may be used to store a set number of images that get replaced as new images are acquired. The method of FIG. 2 may then be continuously performed on the images in this buffer to provide a real-time determination of heart rate during imaging. The number of images stored in this buffer can be selected so that the sampling duration is long enough to capture multiple cardiac cycles. For example, adult humans may potentially have heart rates as low as '30' beats per minute (bpm) (e.g., a cardiac cycle every '2' seconds). To ensure there are enough frames in the buffer for determining the heart rate when performing the method of FIG. 2, the buffer may be selected to store frames for at least '4' seconds (e.g., at least '2' cardiac cycles for an adult human with a '30' bpm heart rate). The number of frames in the buffer that allows for the appropriate sampling duration may vary with the sampling rate. For example, if an ultrasound image feed is being acquired at a frame rate of '30' frames per second (fps), then '120' frames would be needed for a sampling duration of '4' seconds ('30' fps×'4' seconds). To provide more data for the analysis performed in subsequent acts and to enhance accuracy in the determined heart rate, the buffer may be selected to have more than '4' seconds of data. For example, in an example embodiment selected to have '6' seconds of data and where the sampling rate is '30' fps, the buffer may have '180' frames ('30' fps×'6' seconds).

Referring still to act 205 of FIG. 2, in embodiments where the method of FIG. 2 is being performed on a cineloop (e.g., instead of on real-time ultrasound images being acquired live), act 205 may involve reading the ultrasound image frames from the cineloop.

At 210 of FIG. 2, the method involves dividing each ultrasound image of the plurality of ultrasound images into a plurality of regions. When performing this dividing, each region can be positioned so that the region corresponds to a substantially similar region location present across the plurality of ultrasound images acquired at act 205.

Referring simultaneously to FIG. 3, shown there generally as 300 is an illustration of regions that may be positioned on frames of the example ultrasound image feed shown in FIGS. 1A-1D, in accordance with at least one embodiment of the present invention. The regions 302 may form a number of rows 304 and a number of columns 306 covering an ultrasound image (e.g., as illustrated, a '3' row by '5' column grid). This region configuration may be suitable for the example ultrasound image feed of FIGS. 1A-1D because the imaged heart there is an adult image heart. However, in various embodiments, the grid configuration may be modified. For example, to capture the smaller movements of a fetal heart, a finer (e.g., less coarse, and more granular) grid configuration may be possible (e.g., '4' rows by '10' columns).

Since increasing the number of total regions 302 may increase the number of locations on which subsequent acts are to be performed (and correspondingly, the processing requirements to perform embodiments of the present methods), various grid configurations may be used to balance between performance and heart rate accuracy. For example, if the present methods were configured to execute in an environment with limited computing resources and/or where it was known that relatively large physical cardiac anatomical structures were being imaged (e.g., certain veterinarian applications or adult human hearts), a total number of region locations may be configured to be as few as '2' (e.g., a '2×1' or a '1×2' grid). In another example, if the present methods were being configured to execute in an environment where there are fewer restrictions on computing resources and/or if there it was possible that small (e.g., fetal) cardiac structures were being imaged, the total number of region locations can be as many as '50' (e.g., a '5×10' or '10×5' grid).

Referring back to FIG. 2, at 215, for each region location on each of the plurality of ultrasound images, a statistical calculation on image data of the region location may be performed. The statistical calculation may be any suitable statistical parameters that provides information about the image data in a region location. For example, the statistical calculation may be the mean brightness value of the pixels within a given region. In various embodiments, the statistical calculation may include an indication of variation in brightness of the image data of the region location. For example, in some embodiments, the statistical calculation may be the variance or standard deviation of brightness values of the image data of the region location.

Figure 4:
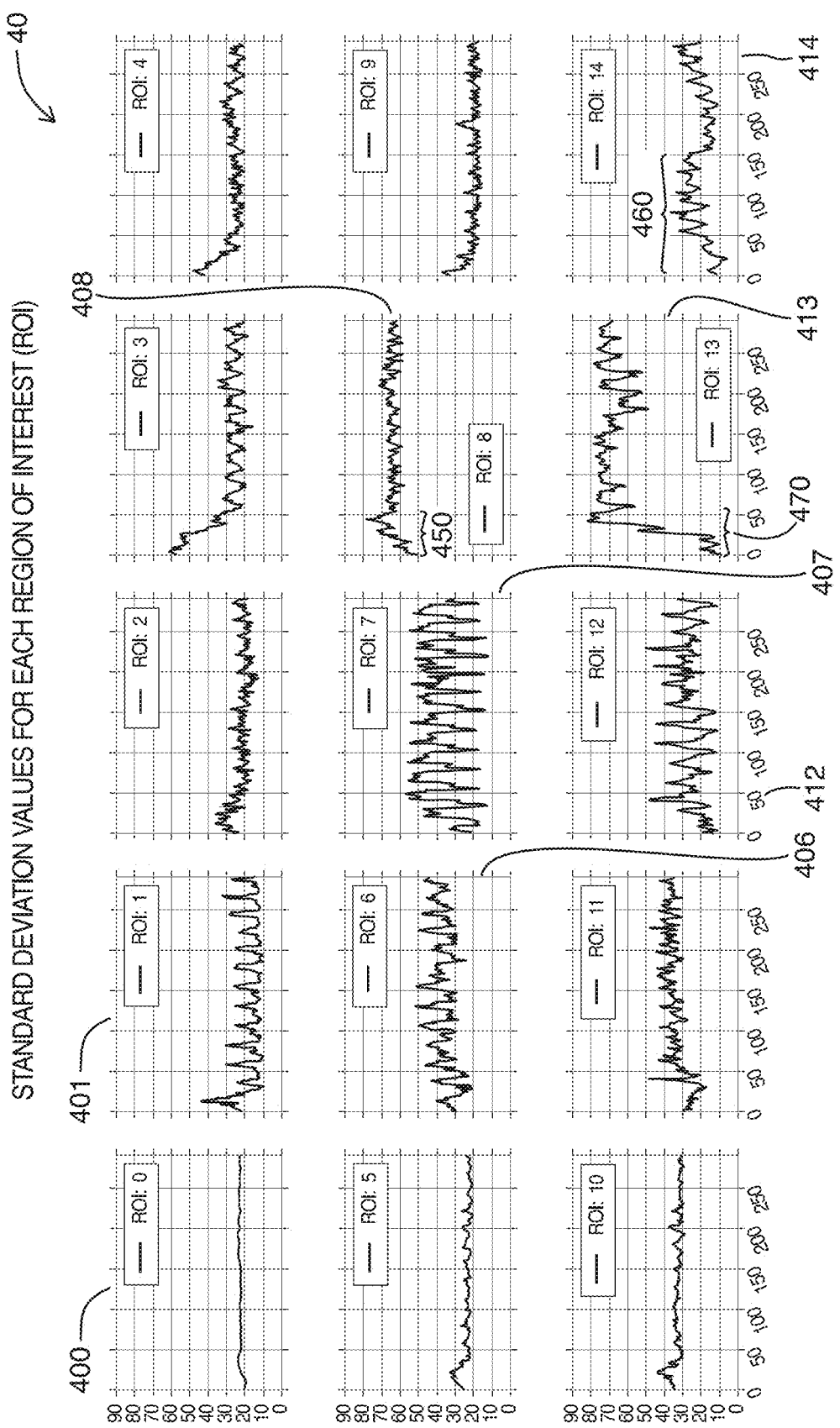
FIG. 4 are charts showing plots of a statistical calculation for each region shown in FIG. 3, over a number of frames of an ultrasound image feed, in accordance with at least one embodiment of the present invention.

Referring simultaneously to FIG. 4, shown there generally as 40 are charts showing plots of a statistical calculation for each region shown in FIG. 3, over a number of frames of the example ultrasound image feed, in accordance with at least one embodiment of the present invention. The X-axis in the plots of FIG. 4 correspond to frame numbers. The plots shown in FIG. 4 are provided in a '3' row by '5' column configuration similar to FIG. 3, where the row by column position of a plot in FIG. 4 corresponds to the same row by column region location in the grid configuration shown in FIG. 3. The plots 40 are for the example video/series of frames from which the screenshots of FIGS. 1A-1D were selected.

In FIG. 4, plot 400 (labeled as 'ROI: 0') shows the calculated standard deviation values of an upper left hand corner region 302 over the series of frames in the example sequence. As shown, it can be seen there is relatively little variation in the standard deviation values over the series of frames. Referring simultaneously back to FIGS. 1A-1D, this is reflected in the top left corner of the screen captures 100a-100d being primarily black, without much variation in the brightness values over the course a cardiac cycle.

Referring still to FIG. 4, plot 401 (labeled as 'ROI: 1') shows more variation in the calculated standard deviation over the course of the example series of frames. Referring again to FIGS. 1A-1D, it can be seen that this is because the region position for plot 401 may have heart anatomical structures come into and out of the region during the course of a cardiac cycle (e.g., in reference also to the corresponding region location shown in FIG. 3, it can be seen that these anatomical structures may enter and exit the region location in the lower right hand corner of the region location).

In various embodiments, if the image data in the region position is primarily black during one phase of the cardiac cycle (either diastole or systole; e.g., because heart anatomical structures are not present in the region), the standard deviation in the region may be low because there is not much variation amongst the brightness values in those frames. However, as the cardiac cycle proceeds to the other phase, a heart anatomical structure may enter the region. This may result in more bright pixels being in the region location, such that there is a broader distribution of brightness values. This would result in the standard deviation of that region location being higher in those frames. The periodic cardiac cycle over a series of frames may thus result in the periodic plot of standard deviation values.

Referring still to FIG. 4, it can be seen that while the periodic motion of cardiac cycles is present on a number of the region locations, the severity of the changes in the standard deviation value is most pronounced in plot 407 (labeled as 'ROI: 7'). This reflects the visual changes in the image data in the underlying series of frames. Referring simultaneously to FIG. 3 and FIGS. 1A-1D, the image data for plot 407 (the vertically center region location in the horizontally middle column) contains an image of the heart valve during various phases of a cardiac cycle. When the heart valve is open, there is generally an absence of bright pixels in the region location (e.g., as is shown at 102b in FIG. 1B). This results in the region location generally appearing dark with low variation in image brightness values, such that a low standard deviation value may be associated with these image frames. In contrast, when the heart valve is closed or about to close, bright structures are generally present in the region location (e.g., as is shown at 102a, 102c, 102d in FIGS. 1A, 1C and 1D respectively). This results in the image data of the region location having generally both dark and bright values, such that there is a relatively high standard deviation value associated with these image frames. Over the systolic and diastolic phases of a cardiac cycle, the transition from a primarily dark region to a region with broad variation in brightness values results in the plot 407 shown in FIG. 4, where there is large variation in the standard deviation values of the image data in the region location over the example series of frames.

Referring still to FIG. 4, plots 406 (labeled as 'ROI: 6') and 412 (labeled as ROI: 12') can be seen exhibiting periodic changes in standard deviation values at a frequency that is similar to that which is shown in plot 407. Referring again to FIGS. 1A-1D, and FIG. 3, it can be seen that the region locations corresponding to these plots 406, 412 are adjacent (e.g., to the left and immediately below) the horizontally and vertically center region location containing the heart valve experiencing the strongest fluctuations in standard deviation values. These adjacent region locations may thus similarly have heart structures enter/appear within the region location and leave/disappear from the region location during diastolic and systolic phases of a cardiac cycle, so as to produce similar periodic fluctuations in standard deviation values over the series of frames.

In FIG. 4, it can further be seen that plots 408 (labeled as 'ROI: 8') and 413 (labeled as 'ROI: 13') have generally high standard deviation values throughout the example series of frames. Referring simultaneously to FIG. 3, these high standard deviation values may be because the corresponding region locations contain bright structures (e.g., a heart wall). As shown via 104a-104d in FIGS. 1A-1D, the heart wall may expand and contract over the course of a cardiac cycle. However, since the movement of the heart wall remains primarily within each region location (without any bright pixels entering/appearing and exiting/disappearing from the region locations), the corresponding plots 408, 413 in FIG. 4 generally fluctuate around a relatively-high standard deviation value without dipping to lower standard deviation values.

As noted, traditional methods of automating heart rate calculations on ultrasound images generally involve automating M-mode operation. For example, these systems may attempt to automate the plotting of bright pixels corresponding to heart structures as they move over a sequence of frames. However, even in systems that use a Fourier transform to identify the frequency of such movement, the bright pixels would generally need to produce a waveform pattern before the Fourier transform can be applied to it. Obtaining a waveform pattern that has a sufficiently strong signal may be difficult because the axis along which the motion of bright pixels traverse may need to be identified. The identification of this axis (e.g., the scan line in traditional M-mode operation) may be difficult and may require re-orientation of the ultrasound scanner to so that heart wall motion moves along such line.

In contrast, the present embodiments analyze a statistical calculation (e.g., a standard deviation calculation) over the image data in a given region location over a series of frames. Analyzing the statistical calculation may provide a more robust algorithm that can monitor changes in the variation of brightness in a region location, without regard to an axis of motion for bright pixels in an image. This may allow the heart rate to be determined more readily whenever an imaged heart is within the view of the series of frames, without the repositioning of the scanner typically needed in traditional automated heart rate calculation methods.

Referring back to FIG. 2, at 220, for each region location, the method may next involve determining a frequency of change in the statistical calculation over the plurality of ultrasound images. As shown in FIG. 4, it can be seen that the plots for the region locations with the predominant heart structure motion experience fluctuations in the statistical calculations (e.g., standard deviation values) over a number of frames. As discussed below in greater detail, this frequency may be used to calculate the heart rate of an imaged heart.

Act 220 may performed in various ways. For example, in some embodiments, one or more peak-to-peak measurements of data in one or more plots 40 may be calculated to determine the frequency of change. In some such embodiments, the peak-to-peak calculations may be selected to be performed on only the plots exhibiting the greatest fluctuations in the statistical calculations (e.g., plot 407, as may identified using suitable mathematical methods).

Additionally or alternatively, act 220 may involve performing a Fourier transform on the statistical calculations of the region location across the plurality of ultrasound images (e.g., the statistical calculations over the ultrasound images would be considered the signal on which the Fourier transform is performed). As a person skilled in the art would understand, performing a Fourier analysis of a given signal may allow decomposition of that signal into constituent frequencies. A resultant power spectrum may allow identification of where the energy in the signal is mostly highly concentrated. As discussed below with respect to FIG. 7, the dominant frequency from the power spectrum can be selected as the frequency of change for a region location.

To enhance robustness of the present methods, an optional act may be performed in some embodiments to filter out frequencies that are not likely to reflect the heart rate of an imaged heart. For example, the heart rate of an adult human is not likely to be below '20' bpm or above '220' bpm, and a fetal heart rate is likely being between '100'-'200' bpm. As a result, any frequency not within this range in the signal for a given region location can be filtered out. In various embodiments, this optional step may involve performing band pass filtering. In the examples discussed below with regards to FIGS. 5 and 6, the band pass filtering is performed before the determining of frequencies of change using a Fourier analysis shown in FIG. 7. However, in various embodiments, it may be possible to perform the band-pass filtering after, or as a part of, the determining of frequencies of change.

Figure 5:
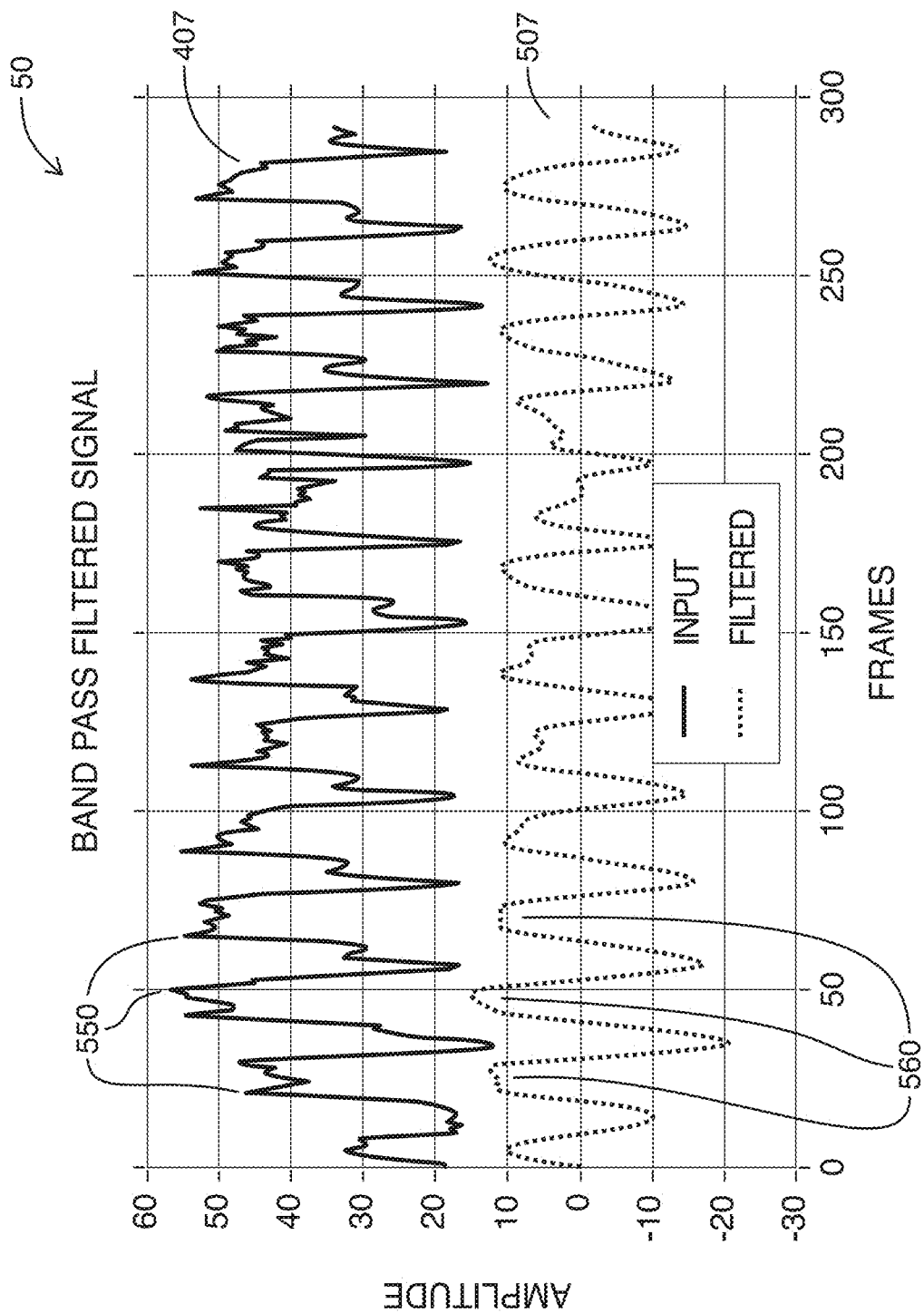
FIG. 5 is a chart showing a plot of a statistical calculation and a corresponding filtered plot, for a given region shown in FIG. 3, and over a number of frames of an ultrasound image feed, in accordance with at least one embodiment of the present invention.

Referring to FIG. 5, shown there generally as 50 is a chart showing a plot of a statistical calculation and a corresponding plot of its band pass filtered signal over a number of frames, for a given region shown in FIG. 3, in accordance with at least one embodiment of the present invention. In FIG. 5, the plot shown in a solid dark line corresponds to the plot 407 shown in FIG. 4. As can be seen, there are a number of high frequency components 550 in the underlying signal that may be present (e.g., due to noise and/or speckle). The plot 507 in FIG. 5 (shown in dotted line) shows the result of performing a band pass filter on the signal of plot 407 to filter out frequencies that are unlikely to reflect the heart beat of an imaged heart. As can be seen, the high frequency components 550 of the signal in plot 407 has been filtered out in the plot 507, such that the areas 560 where the plot would contain high frequency components 550 are smoothed out. In the example plots of FIG. 5, the filtered plot 507 is also normalized around a '0' amplitude on the Y-axis to provide a clear visualization of the filtered plot 507 against the original plot 407.

Figure 6:
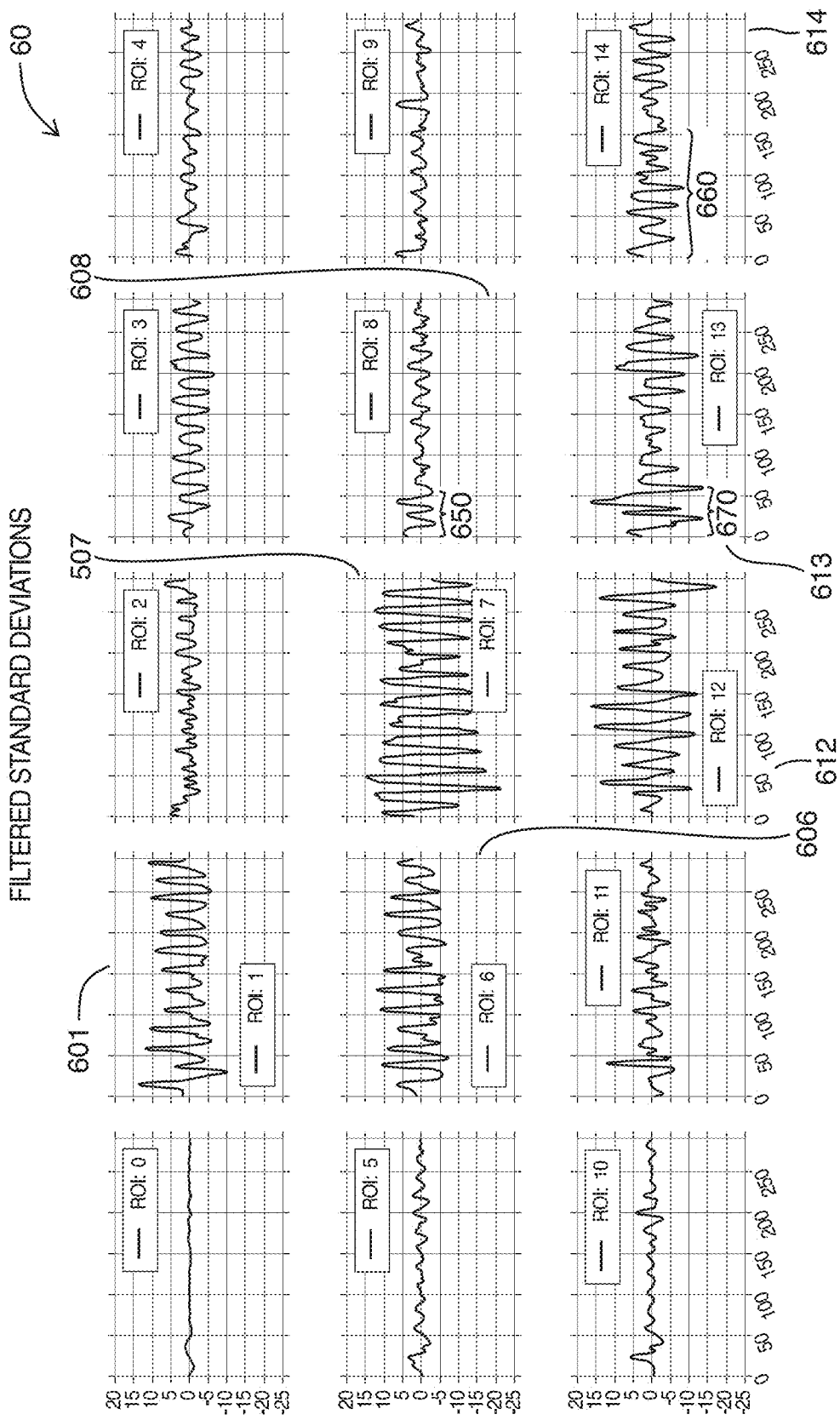
FIG. 6 are charts showing filtered plots of the statistical calculations shown in FIG. 4, for each region shown in FIG. 3, in accordance with at least one embodiment of the present invention.

Referring to FIG. 6, shown there generally as 60 are charts showing plots of band pass filtered versions of the statistical calculations shown in FIG. 4, for each region shown in FIG. 3, in accordance with at least one embodiment of the present invention. Each of the plots 60 in FIG. 6 correspond to plots in the same row and column position shown in FIG. 4, except that the plots shown in FIG. 6 have been band pass filtered, and normalized around a '0' amplitude on the Y-axis.

Referring simultaneously to FIGS. 4 and 6, it can be seen that a number of the frequencies that are too low or too high to represent heart rates have been filtered out in the plots 60 of FIG. 6. For example, when comparing plots 606, 601, 612 in FIG. 6 to their counterpart plots 406, 401, 412 in FIG. 4, it can be seen that a number of the higher frequency components have been filtered out—in a manner similar to plot 507 and 407 discussed above in FIG. 5 (plot 507 is also viewable in the vertically center plot in the middle column of FIG. 6). Similarly, when comparing plots 608, 613, 614 in FIG. 6 to plots 408, 413, 414 in FIG. 4, it can be seen that the lower frequency components 450, 470, 460 present in the plots 408, 413, 414 of FIG. 4 are no longer present in the corresponding areas 650, 670, 660 in the plots 608, 613, 614 of FIG. 6.

As the lower frequency components may be due to the initial movement of the scanner that positions the imaged heart into the field of view, filtering out the lower frequencies in this optional step, while not required, may facilitate ease of identifying the dominant determined frequency in subsequent acts. Similarly, filtering out the high frequencies present in the original plots 40 of FIG. 4 may also facilitate ease of identifying the dominant determined frequency in subsequent acts because high frequency signals present in the plots 40 of FIG. 4 may represent noise and/or speckle.

Referring back to FIG. 2, after act 220 and an optional act of performing a band pass filter (not shown in FIG. 2), the method may proceed to determine the region location having a dominant determined frequency of change in the statistical calculation over the plurality of ultrasound images (act 225). For example, in embodiments where a Fourier transform is performed to identify the dominant frequency, this may involve selecting the region location, of the plurality of regions, having the highest magnitude for the frequency of change.

Figure 7:
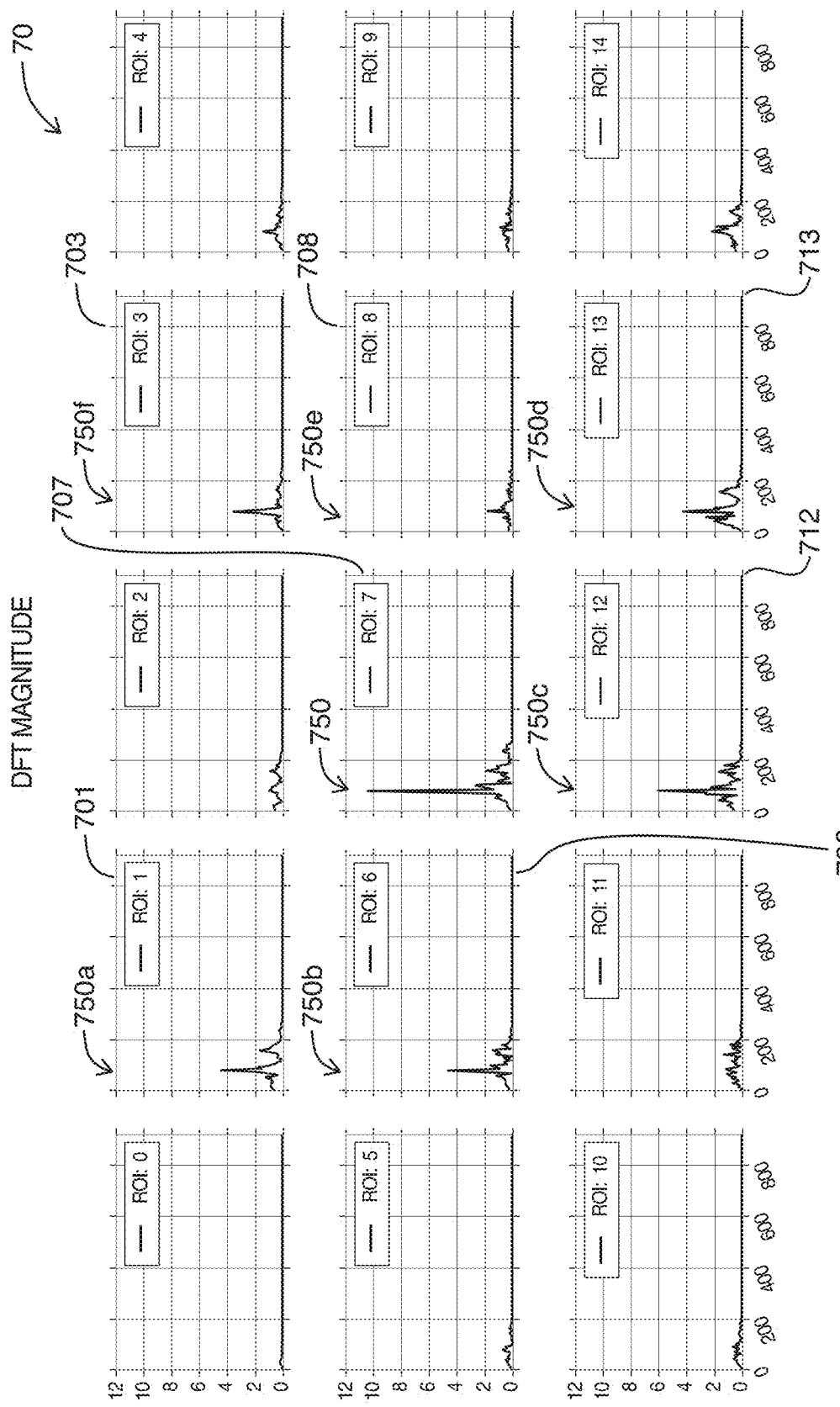
FIG. 7 are charts showing plots of frequencies present on the filtered plots of FIG. 6, for each region shown in FIG. 3, in accordance with at least one embodiment of the present invention.
Figure 8:
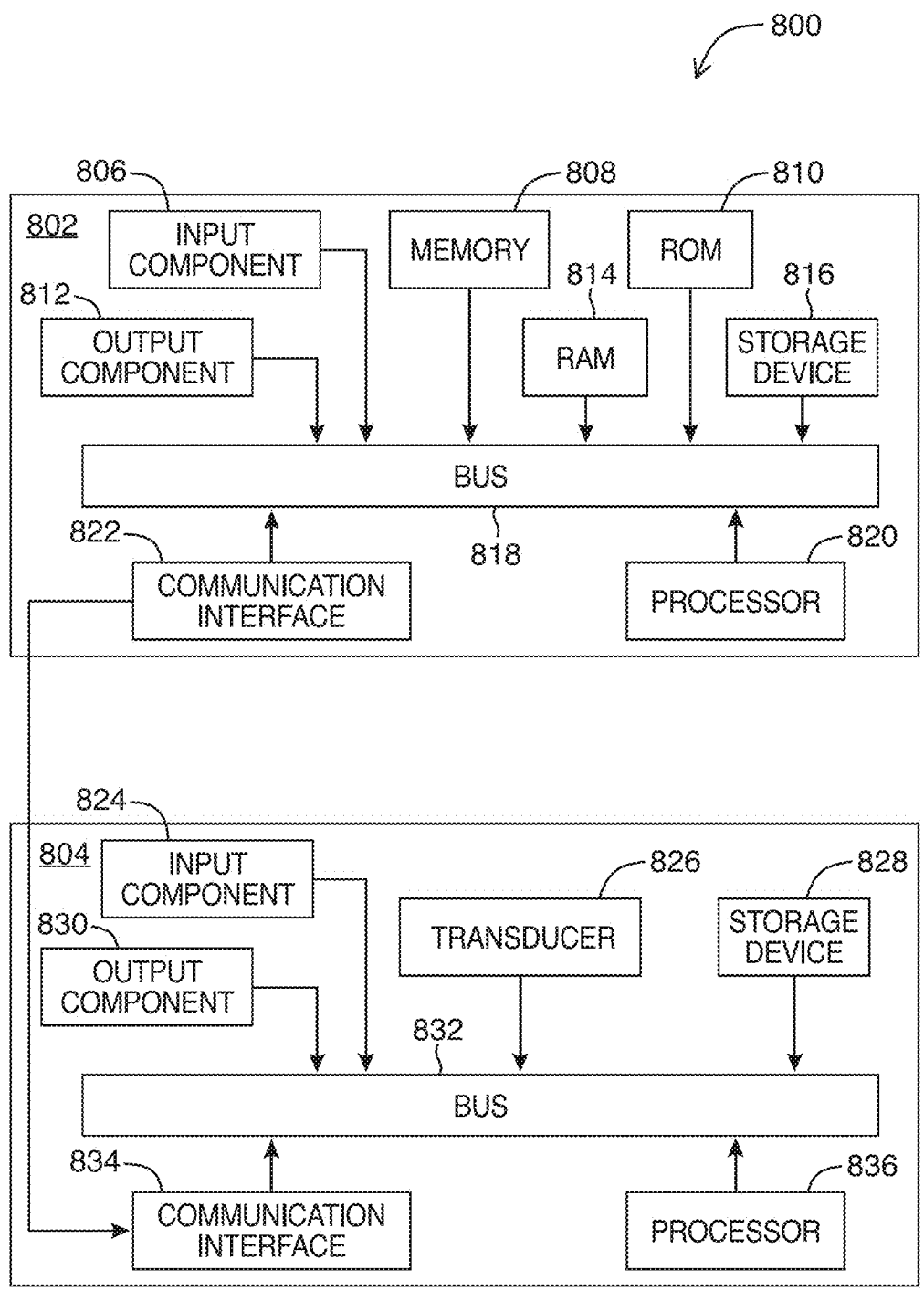
FIG. 8 shows a functional block diagram of an ultrasound system, in accordance with at least one embodiment of the present invention.

Referring to FIG. 7, shown there generally as 70 are plots of frequencies present on the band pass filtered versions of the statistical calculations shown in FIG. 6, for each region shown in FIG. 3, in accordance with at least one embodiment of the present invention. Each of the plots 70 correspond to plots in the same row and column position shown in FIGS. 6 and 4. However, plots 70 shown in FIG. 7 show the magnitudes resulting from a Fourier analysis (e.g., a Discrete Fourier Transform (DFT)) on the plots 60 shown in FIG. 6.

In FIG. 7, it can be seen that of all the plots 70, plot 707 (for 'ROI: 7') has the highest magnitude value at a frequency 750 around '80' on the X-axis. In the example embodiment, the region location corresponding to plot 707 can thus be selected as the region location having the highest magnitude for the frequency of change.

It can also be seen that in FIG. 7, there are a number of different plots also having peaks at a substantially similar frequency (e.g., near '80' on the X-axis). For example, this common peak frequency can be seen at least in plots 701, 706, 712, 713, 708, and 703, where the peak frequencies are variously highlighted as 750*a*-750*f*. As discussed above, these various plots having a similar peak frequency may be due to the region locations corresponding to these plots experiencing similar fluctuations in the statistical calculation (but to a lesser degree) as the region location (e.g., 'ROI: 7') with the highest such fluctuations.

While various plots 70 in FIG. 7 may have similar peak frequencies (and thus may potentially also be used to identify the frequency for calculating the heart rate of the imaged heart), selecting the plot and region location (e.g., plot 707 in FIG. 7) with the highest magnitude for the peak frequency may enhance confidence that the frequency ultimately selected for calculating the heart rate of the imaged heart is accurate.

For example, while in the example series of frames analyzed in FIG. 7, there are other plots that also have substantially similar peak frequencies, the difference between the magnitude values at different frequencies in these plots are generally less pronounced. Depending on the underlying series of ultrasound image frames, it is possible that the peak frequency in these other plots may not in fact reflect the heart rate of an imaged heart. For example, because the difference between the magnitude values at different frequencies is smaller, the frequency representative of the heart rate may potentially be dominated by another frequency (e.g., from noise or other structural movements captured in the images). Selecting the peak frequency from one of these other plots may therefore potentially result in a less accurate (e.g., potentially mistaken) determination of the frequency corresponding to the heart rate.

In contrast, by selecting the region location with the highest magnitude, the present methods can focus on the region location having the most pronounced/severe periodic motion within the image. Even if other region locations have other types of periodic motion with lesser severity, it is the most pronounced periodic motion that is likely to reflect the heart rate of an imaged heart over a series of ultrasound frames. In the present embodiments, the selection of the region location with the highest magnitude for the peak frequency may thus allow for more robust operation; e.g., the methods can be used on ultrasound frame sequences containing not only an imaged heart but also other incidental structures with motion (which would be dismissed when determining the heart rate).

The plots 70 of FIG. 7 show the result of a Fourier analysis on the band pass filtered plots of FIG. 6. However, in various embodiments, it is possible to perform the Fourier transform on the original plots of the statistical calculation that have not had the optional step of band pass filtering performed (e.g., the plots 40 shown in FIG. 4 in the example series of frames discussed herein). For example, in some embodiments, the methods discussed herein may be robust enough to not require the optional band-pass filtering act.

This is because selection of the region location with the highest magnitude for the frequency of change in act 225 of FIG. 2 can avoid mistaken selection of frequencies that do not correspond to the periodic motion of the heart rate, since those other non-heart-rate frequencies may generally be less pronounced when compared to the dominant periodic motion of a heart beating.

Referring back to FIG. 2, the method may next proceed to act 230 to identify the selected region location having the dominant determined frequency as a region of interest (ROI). After having identified the ROI, the method may proceed to act 235 and calculate the heart rate based on the determined frequency of change of the ROI. In some embodiments, this calculating may involve translating the dominant determined frequency of change from a per-frame basis to a per-unit-time basis. For example, this translating may be performed based on a frame rate of the ultrasound image feed.

As illustrated in FIG. 7, the values along the X-axis are shown as having already been calculated to be in units of beats per minute (bpm), such that the peak frequency at '80' for the region location (corresponding to plot 707) having the highest magnitude in the Fourier analysis corresponds to a heart rate of '80' bpm. However, in some embodiments, the units of the plot of the Fourier analysis may instead correspond to the number of frames analyzed. In these embodiments, the peak for the Fourier analysis may be identified at a given frame along the sequence of frames. To calculate a meaningful heart rate in these embodiments, the peak value at this frame number may be divided by the length of frames used for the Fourier analysis (e.g., a Fast Fourier Transform (FFT) length—as will be apparent to persons skilled in the art, this is a parameter that is the closest power of '2' to the number of frames in the ultrasound sequence of frame being analyzed). The result can then be multiplied by the sampling rate (typically this is the frame rate, in units of frames per second (fps)). The result may then be multiplied by '60' (seconds per minute) to arrive at a meaningful bpm heart rate.

Modifications to the methods discussed herein may be possible in various embodiments. For example, as discussed above, the region location with the highest magnitude is selected as the region location from which to identify the dominant frequency for calculating heart rate. However, in alternative embodiments, the frequency for calculating the heart rate may be identified in a different manner. As noted with respect to FIG. 7, a number of different region locations can have substantially the same peak frequency. Thus, in some alternative embodiments, the prevalence of a peak frequency can be used as a way for identifying the frequency for calculating the heart rate. For example, this may involve identifying the most common peak frequency amongst the different region locations, and using it as the dominant frequency for calculating the heart rate. These embodiments may, for example, be suitable when determining the heart rate of an adult heart (e.g., as compared to a fetal heart), where periodic motion for a cardiac cycle may be present in multiple region locations.

Additionally or alternatively, an average magnitude spectrum can be calculated by using region locations where the magnitude of the spectrum is higher than a certain threshold. The peak frequency may then be selected from the average magnitude spectrum; either as an independent determination of the dominant frequency or as a confirmation of a dominant frequency calculated in a different manner.

In another example modification, prior to the dividing the plurality of ultrasound images into regions (act 210 in FIG.

2), one or more of the plurality of the images may be scaled down. Scaling down the images may make the various image processing acts subsequent to act 210 more efficient, and reduce the computational resources required to perform the present methods. For example, this may better facilitate the performance of the present methods on ultrasound scanners with limited real-time processing capabilities, such as on handheld wireless ultrasound scanners.

Referring to FIG. 8, shown there generally as 800 is a functional block diagram of an ultrasound system, in accordance with at least one embodiment of the present invention. For example, the ultrasound imaging system 800 (or any individual apparatus or device included therein) may be configured to perform the method of FIG. 2 to determine a heart rate of an imaged heart in an ultrasound image feed.

Ultrasound imaging system 800 may include a number of different apparatus or computing devices. As illustrated, ultrasound imaging system 800 includes an ultrasound acquisition unit 804 configured to transmit ultrasound energy to a target object, receive ultrasound energy reflected from the target object, and generate ultrasound image data based on the reflected ultrasound energy. The ultrasound acquisition unit 804 may include a transducer 826 which converts electric current into ultrasound energy and vice versa. Transducer 826 may transmit ultrasound energy to the target object which echoes off the tissue. The echoes may be detected by a sensor in transducer 826 and relayed through a bus 832 to a processor 836. Processor 836 may interpret and process the echoes to generate image data of the scanned tissue. In some embodiments, the ultrasound acquisition unit 804 (or various components thereof) may be provided as a handheld ultrasound probe or scanner that is in communication with other components of the ultrasound imaging system 800. For example, the handheld probe may include the transducer 826 of ultrasound acquisition unit 804. Ultrasound acquisition unit 804 may also include storage device 828 (coupled to and accessible by bus 832) for storing software or firmware instructions, configuration settings (e.g., sequence tables), and/or ultrasound image data.

Although not illustrated, as will be apparent to one of skill in the art, the ultrasound imaging system 800 may include other components for acquiring, processing and/or displaying ultrasound image data. These include, but are not limited to: a scan generator, transmit beamformer, pulse generator, amplifier, analogue to digital converter (ADC), receive beamformer, signal processor, data compressor, wireless transceiver and/or image processor. Each of these may be components of ultrasound acquisition unit 804 and/or electronic display unit 802 (described below).

Ultrasound imaging system 800 may include an electronic display unit 802 which is in communication with ultrasound acquisition unit 804 via communication interfaces 822/834. In various embodiments, communication interfaces 822/834 may allow for wired or wireless connectivity (e.g., via Wi-Fi™ and/or Bluetooth™) between the electronic display unit 802 and the ultrasound acquisition unit 804. Electronic display unit 802 may work in conjunction with ultrasound acquisition unit 804 to control the operation of ultrasound acquisition unit 804 and display the images acquired by the ultrasound acquisition unit 804. An ultrasound operator may interact with the user interface provided by display unit 802 to send control commands to the ultrasound acquisition unit 804 (e.g., to initiate an operation mode that initiates execution of the methods for determining a heart rate described herein). The electronic display unit 802 may be a portable device, which may include a mobile computing device (e.g. smartphone), tablet, laptop, or other suitable device incorporating a display and a processor and capable of accepting input from a user and processing and relaying the input to control the operation of the ultrasound acquisition unit 804 as described herein.

Each of ultrasound acquisition unit 804 and display unit 802 may have one or more input components 824, 806 and/or one or more output components 830, 812. In the FIG. 8 embodiment, ultrasound acquisition unit 804 may include an input component 824 which is configured to accept input from the user (e.g., to turn on the ultrasound acquisition unit 804 or control the connection of the ultrasound acquisition unit 804 to the electronic display unit 802). For example, in some embodiments, ultrasound acquisition unit 804 may also include an output component 830, such as a LED indicator light which can output the status of the ultrasound acquisition unit 804.

In the FIG. 8 embodiment, display unit 802 may include an input component 806 configured to accept input from the user. Certain input received at input component 806 may be relayed to ultrasound acquisition unit 804 to control the operation of ultrasound acquisition unit 804. Display unit 802 may also include an output component 812, such as a display screen, which displays images based on image data acquired by ultrasound acquisition unit 804. In particular embodiments, display unit 802's input component 806 may include a touch interface layered on top of the display screen of the output component 812. Electronic display unit 802 may also include memory 808, Random Access Memory (RAM) 814, Read Only Memory (ROM) 810, and persistent storage device 816, which may all be connected to bus 818 to allow for communication therebetween and with processor 820. Ultrasound acquisition unit 804 may contain memory (e.g., storage device 828) that may be accessible by processor 836. Any number of these memory elements may store software or firmware that may be accessed and executed by processor 820 and/or processor 836 to, in part or in whole, perform the acts of the methods described herein (e.g., so that the processor 820 and/or processor 836 is configured to perform the methods described herein to determine a heart rate of an imaged heart in an ultrasound image feed).

In some embodiments, all of the input controls and display screen necessary for the operation of the ultrasound imaging system 800 may be provided by input and output components 806, 812 of the display unit 802. In such cases input and output components 824, 830 of ultrasound acquisition unit 804 may be optional and/or omitted. In certain embodiments, the ultrasound acquisition unit 804 may be a handheld probe (i.e. including transducer 826) which is in communication with the display unit 802 over the communications interfaces 822/834 to facilitate operation of the ultrasound acquisition unit 804 and processing and display of ultrasound images.

In various embodiments, at least a portion of the processing of the image data corresponding to the reflected ultrasound energy detected by the handheld probe's transducer 826 may be performed by one or more of processors internal to the ultrasound acquisition unit 804 (such as by the processor 836) and/or by processors external to the ultrasound acquisition unit 804 (such as the processor 820 of electronic display unit 802). By having some of the image data processing tasks typically performed by a processor 836 of ultrasound acquisition unit 804 be performed instead by a processor 820 of the display unit 802, less physical processing hardware may need to be provided on the ultrasound acquisition unit 804. This may facilitate a lightweight, portable design and construction for the ultrasound acquisition unit 804 (e.g., when it is a handheld probe). In particular embodiments the handheld probe may have a mass that is less than approximately 1 kg (2 lbs).

In some embodiments, the output component 830 of ultrasound acquisition unit 804 may include a display screen, which can be configured to display or otherwise output the images acquired by ultrasound acquisition unit 804 (in addition to or alternative to displaying such images on the display unit 802).

As noted, the ultrasound imaging system 800 of FIG. 8 may be configured to perform the method of FIG. 2, so as to determine a heart rate of an imaged heart in an ultrasound image feed. Steps of method 200 in FIG. 2 may be implemented as software or firmware contained in: a program memory 808, 814, 810 or storage device 816 accessible to a processor 820 of display unit 802, and/or a storage device 828 accessible to processor 836 of ultrasound acquisition unit 804. Processor 820/836 may independently or collectively implement various acts of method 200 of FIG. 2 by executing software instructions provided by the software.

Scan conversion is a process that converts image data to allow it to be displayed in a form that is more suitable for human visual consumption. For example, this may involve converting the image data from the data space (e.g. polar coordinate form) to the display space (e.g. Cartesian coordinate form). Depending on the location of where the methods of the present embodiments are performed, the ultrasound images on which the methods are performed may differ. For example, if the methods described herein are performed by processor 836 on the ultrasound acquisition unit 804, the ultrasound images on which the methods may be performed may be pre-scan-converted data. Additionally or alternatively, if the methods described herein are performed by processor 820 on the display unit 802, the methods described herein may be performed on post-scan-converted data.

Figure 9:
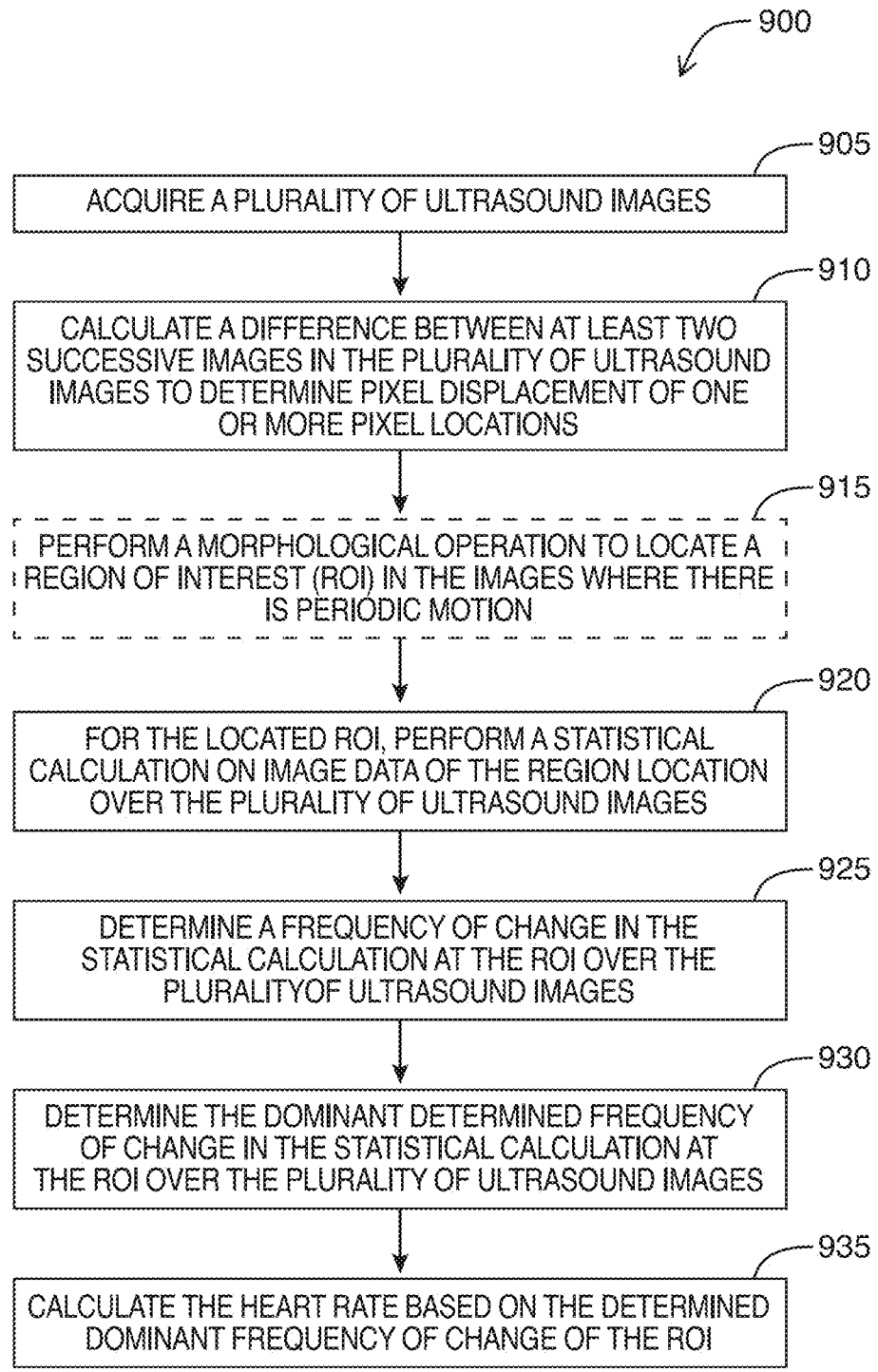
FIG. 9 is a flowchart for a method of determining a heart rate of an imaged in an ultrasound image feed, in accordance with at least one embodiment of the present invention.

Referring to FIG. 9, shown there generally as 900 is a method of determining a heart rate of an imaged in an ultrasound image feed, in accordance with at least one embodiment of the present invention. As discussed below, some acts of method 900 in FIG. 9 are analogous to acts discussed above with respect to FIG. 2.

At 905, a plurality of ultrasound images may be acquired. This act may be performed like act 205 in FIG. 2 discussed above.

At 910, a difference between at least two successive images in the plurality of ultrasound images may be calculated to determine pixel displacement of one or more pixel locations. This may involve analyzing the values of some or all X, Y pixel locations across multiple images in the plurality of ultrasound images, to determine how structures/objects within the images experience motion over the course of the ultrasound image feed. For example, in the calculated difference, pixel locations where there is no motion will generally be zero or black. However, pixel locations with motion will generally appear to have some values. Once the X, Y locations experiencing motion are identified, the method may proceed to act 915.

At 915 (shown in dotted outline), an optional morphological operation may be performed to locate a region of interest (ROI) in the images where there is periodic motion. In various embodiments, the morphological operation may be any suitable mathematical morphology operation that assists in localizing the motion to a common region on the ultrasound images. Various example morphological operations that may be used include erosion, dilation, opening, and closing. As the identified X,Y positions having motion from act 210 may be at various locations on the images, performing a morphological operation may help to localize and consolidate the various X,Y positions into a common region for the purpose of identifying an ROI.

Act 915 is optional and may be omitted. However, since simply calculating the difference between two successive frames in act 910 may potentially result in a large number of X,Y pixel positions experiencing motion, performing the optional morphological operation at act 915 can allow identification of pixel positions that experience relatively large amounts of motion. For example, a morphological operation (e.g., to dilate or open X,Y positions experiencing motion) may consolidate X,Y positions that are proximate to each other, so as to identify an ROI. In this manner, the morphological operation may serve to filter out the pixel locations experiencing less motion.

In various embodiments, the method of FIG. 9 may be performed on ultrasound image feeds containing imaged fetal hearts. Since fetal heart structures are relatively smaller, the motion of the fetal heart is typically localized to a given region of the ultrasound image feed. The method of FIG. 9 can then identify the large motion of the fetal heart, and filter out the lesser motion of other imaged areas.

At 920, for the identified ROI, a statistical calculation on the image data of the region location may be performed over the plurality of the ultrasound images. This act may be performed like the performance of a statistical calculation discussed above in relation to act 215 of FIG. 2. However, whereas act 215 in FIG. 2 involves performing the statistical calculation on multiple region locations, act 920 involves performing the statistical calculation on the ROI identified at act 915 (if the optional act is performed) or an ROI determined from act 910.

At 925, a frequency of change in the statistical calculation at the ROI over the plurality of ultrasound images can be determined. This act may be performed like act 220 in FIG. 2 is performed for a given region location (e.g., on a plot of the statistical calculation values across the plurality of ultrasound images).

At 930, the method may involve determining the dominant determined frequency of change in the statistical calculation at the ROI over the plurality of ultrasound images. This act may be performed like act 225 in FIG. 2 is performed for a given region location. For example, a Fourier analysis may be performed on a plot of the statistical calculation (e.g., a standard deviation calculation) over the image frames. A dominant frequency may then be identified from the frequency corresponding to the highest (e.g., peak) magnitude of the Fourier analysis.

At 935, the heart rate may be calculated based on the determined dominant frequency of change of the ROI. This act may be performed like act 235 discussed above with respect to FIG. 2.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

INTERPRETATION OF TERMS

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method of determining a heart rate of an imaged heart in an ultrasound image feed, the method comprising:
   acquiring a plurality of ultrasound images;
   for each ultrasound image of the plurality of ultrasound images, dividing the image into a plurality of regions, wherein each region is positioned so that the region corresponds to a region location present across the plurality of ultrasound images;
   for each region location on each of the plurality of ultrasound images, performing a statistical calculation on image data of the region location;

for each region location, determining a frequency of change in the statistical calculation over the plurality of ultrasound images;

determining the region location having a dominant determined frequency of change in the statistical calculation over the plurality of ultrasound images;

identifying a selected region location having the dominant determined frequency as a region of interest (ROI); and calculating the heart rate based on the determined frequency of change of the ROI.

2. The method of claim 1, wherein the statistical calculation comprises an indication of variation in brightness of the image data of the region location.

3. The method of claim 2, wherein the statistical calculation comprises a standard deviation of brightness values of the image data of the region location.

4. The method of claim 1, wherein when determining the frequency of change for each region location over the plurality of ultrasound images, the method further comprises:

performing a Fourier transform on the statistical calculations of the region location across the plurality of ultrasound images, to generate a power spectrum; and selecting a peak frequency from the power spectrum as the frequency of change for the region location.

5. The method of claim 1, wherein when determining the region location having the dominant determined frequency of change in the statistical calculation, the method further comprises:

selecting the region location, of the plurality of regions, having the highest magnitude for the frequency of change.

6. The method of claim 1, further comprising:

prior to the dividing, scaling down at least one ultrasound image of the plurality of ultrasound images.

7. The method of claim 1, wherein the plurality of regions forms a grid.

8. The method of claim 1, wherein a total number of region locations is less than 50.

9. The method of claim 1, wherein a total number of region locations is at least 2.

10. The method of claim 1, further comprising:

performing a band pass filter on at least one determined frequency of a region location to eliminate non-heart-rate frequencies.

11. The method of claim 1, wherein the calculating the heart rate comprises:

translating the dominant determined frequency of change from a per-frame basis to a per-unit-time basis, and wherein the translating is performed based on a frame rate of the ultrasound image feed.

12. An ultrasound imaging apparatus for determining a heart rate of an imaged heart in an ultrasound image feed, the apparatus comprising:

a processor; and a memory storing instructions for execution by the processor, wherein when the instructions are executed by the processor, the processor is configured to:

acquire a plurality of ultrasound images;

for each ultrasound image of the plurality of ultrasound images, divide the image into a plurality of regions, wherein each region is positioned so that the region corresponds to a region location present across the plurality of ultrasound images;

for each region location on each of the plurality of ultrasound images, perform a statistical calculation on image data of the region location;

for each region location, determine a frequency of change in the statistical calculation over the plurality of ultrasound images;

determine the region location having a dominant determined frequency of change in the statistical calculation over the plurality of ultrasound images;

identify a selected region location having the dominant determined frequency as a region of interest (ROI); and calculate the heart rate based on the determined frequency of change of the ROI.

13. The ultrasound imaging apparatus of claim 12, wherein the statistical calculation comprises a standard deviation of brightness values of the image data of the region location.

14. The ultrasound imaging apparatus of claim 12, wherein when determining the frequency of change for each region location over the plurality of ultrasound images, the processor is further configured to:

perform a Fourier transform on the statistical calculations of the region location across the plurality of ultrasound images, to generate a power spectrum; and select a peak frequency from the power spectrum as the frequency of change for the region location.

15. The ultrasound imaging apparatus of claim 12, wherein when determining the region location having the dominant determined frequency of change in the statistical calculation, the processor is further configured to:

select the region location, of the plurality of regions, having the highest magnitude for the frequency of change.

16. The ultrasound imaging apparatus of claim 12, wherein the processor is further configured to:

prior to the dividing, scale down at least one ultrasound image of the plurality of ultrasound images.

17. The ultrasound imaging apparatus of claim 12, wherein the processor is further configured to:

perform a band pass filter on at least one determined frequency of a region location to eliminate non-heart-rate frequencies.

18. A non-transitory computer readable medium storing instructions for determining a heart rate of an imaged heart in an ultrasound image feed, the instructions for execution by a processor of a computing device, wherein when the instructions are executed by the processor, the processor is configured to:

acquire a plurality of ultrasound images;

for each ultrasound image of the plurality of ultrasound images, divide the image into a plurality of regions, wherein each region is positioned so that the region corresponds to a region location present across the plurality of ultrasound images;

for each region location on each of the plurality of ultrasound images, perform a statistical calculation on image data of the region location;

for each region location, determine a frequency of change in the statistical calculation over the plurality of ultrasound images;

determine the region location having a dominant determined frequency of change in the statistical calculation over the plurality of ultrasound images;

identify a selected region location having the dominant determined frequency as a region of interest (ROI); and calculate the heart rate based on the determined frequency of change of the ROI.

19. The computer readable medium of claim 18, wherein the statistical calculation comprises a standard deviation of brightness values of the image data of the region location.

20. The computer readable medium of claim 18, wherein when determining the frequency of change for each region location over the plurality of ultrasound images, the instructions further configure the processor to:
perform a Fourier transform on the statistical calculations of the region location across the plurality of ultrasound images, to generate a power spectrum; and
select a peak frequency from the power spectrum as the frequency of change for the region location.

\* \* \* \* \*